United States Patent
Bazille

(10) Patent No.: US 10,512,491 B2
(45) Date of Patent: Dec. 24, 2019

(54) SURGICAL ASSEMBLY FOR PLACING A PEDICLE-SCREW CAP

(71) Applicant: Spineway, Ecully (FR)

(72) Inventor: Julien Bazille, Lyons (FR)

(73) Assignee: Spineway, Ecully (FR)

( * ) Notice: Subject to any disclaimer, the term of this patent is extended or adjusted under 35 U.S.C. 154(b) by 142 days.

(21) Appl. No.: 15/746,804

(22) PCT Filed: Aug. 8, 2016

(86) PCT No.: PCT/FR2016/052049
§ 371 (c)(1),
(2) Date: Jan. 23, 2018

(87) PCT Pub. No.: WO2017/032938
PCT Pub. Date: Mar. 2, 2017

(65) Prior Publication Data
US 2019/0083150 A1 Mar. 21, 2019

(30) Foreign Application Priority Data
Aug. 27, 2015 (FR) ..................... 15 57966

(51) Int. Cl.
*A61B 17/70* (2006.01)
*A61B 17/86* (2006.01)
(52) U.S. Cl.
CPC ...... *A61B 17/7091* (2013.01); *A61B 17/7001* (2013.01); *A61B 17/8605* (2013.01)
(58) Field of Classification Search
CPC .. A61B 17/70; A61B 17/7091; A61B 17/7001
See application file for complete search history.

(56) References Cited

U.S. PATENT DOCUMENTS

| 2014/0214097 A1* | 7/2014 | Jackson | A61B 17/7037 606/305 |
| 2014/0276896 A1* | 9/2014 | Harper | A61B 17/7086 606/104 |

FOREIGN PATENT DOCUMENTS

| FR | 2863861 | 6/2005 |
| WO | WO 94/26190 | 11/1994 |
| WO | WO 00/22997 | 4/2000 |

(Continued)

OTHER PUBLICATIONS

International Search Report and the Written Opinion dated Nov. 10, 2016 From the International Searching Authority Re. Application No. PCT/FR2016/052049. (11 Pages).

*Primary Examiner* — Christopher J Beccia

(57) ABSTRACT

The invention relates to a surgical assembly which comprises: a cap (2) comprising an outer thread (2c) and a central recess for inserting a screw bit; a cap-holder in the form of a hollow sleeve (10) comprising a connection end (11) for connecting with the cap (2), and a locking pin (15) slidably mounted in the hollow sleeve (10) between a neutral position and a locking position of the cap; the cap (2) comprises at least two diametrically opposed radial notches (7), arranged away from an outer side wall of said cap (2), each of the notches (7) comprising at least one side groove (8); the connection end (11) is extended longitudinally by two diametrically opposed lugs (12) capable of being inserted into the notches (7) and each including a side shoulder (12a) which complements the groove (8) of the notch (7) capable of being inserted into said groove in order to lock the sleeve (10) axially onto the cap.

8 Claims, 4 Drawing Sheets

(56) References Cited

FOREIGN PATENT DOCUMENTS

| WO | WO 2008/134758 | 11/2008 |
| WO | WO 2017/032938 | 3/2017 |

* cited by examiner

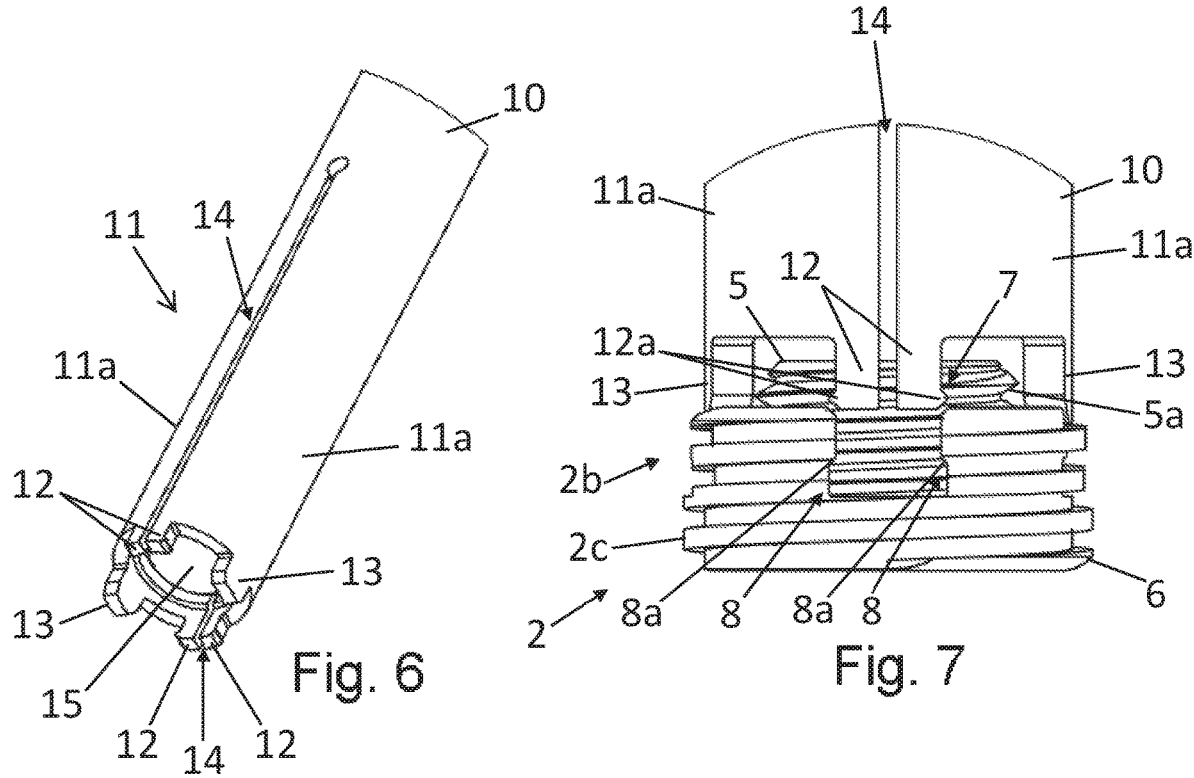
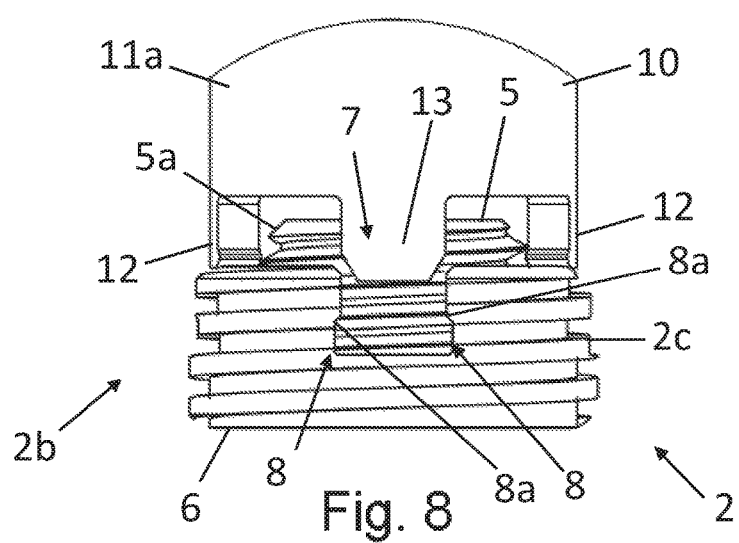

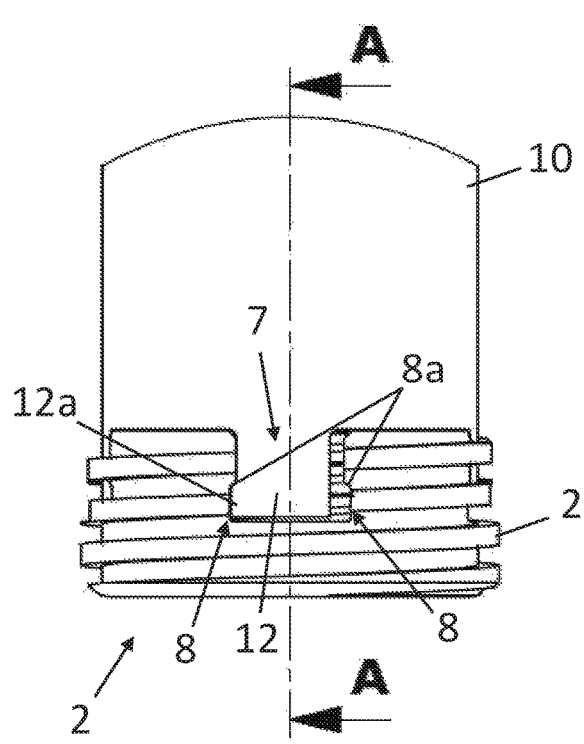
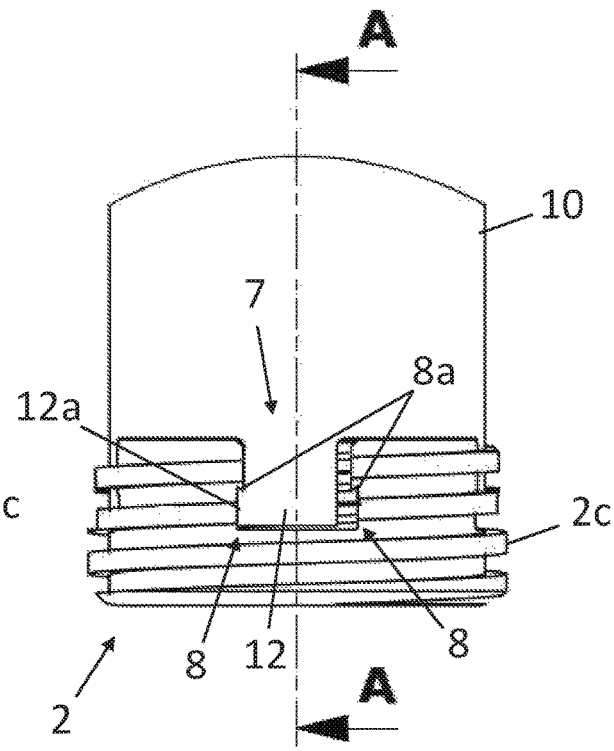
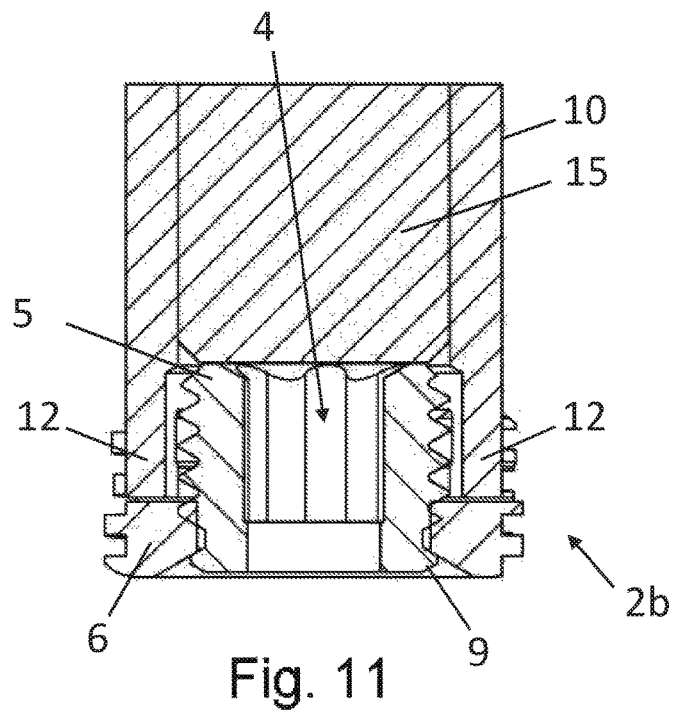

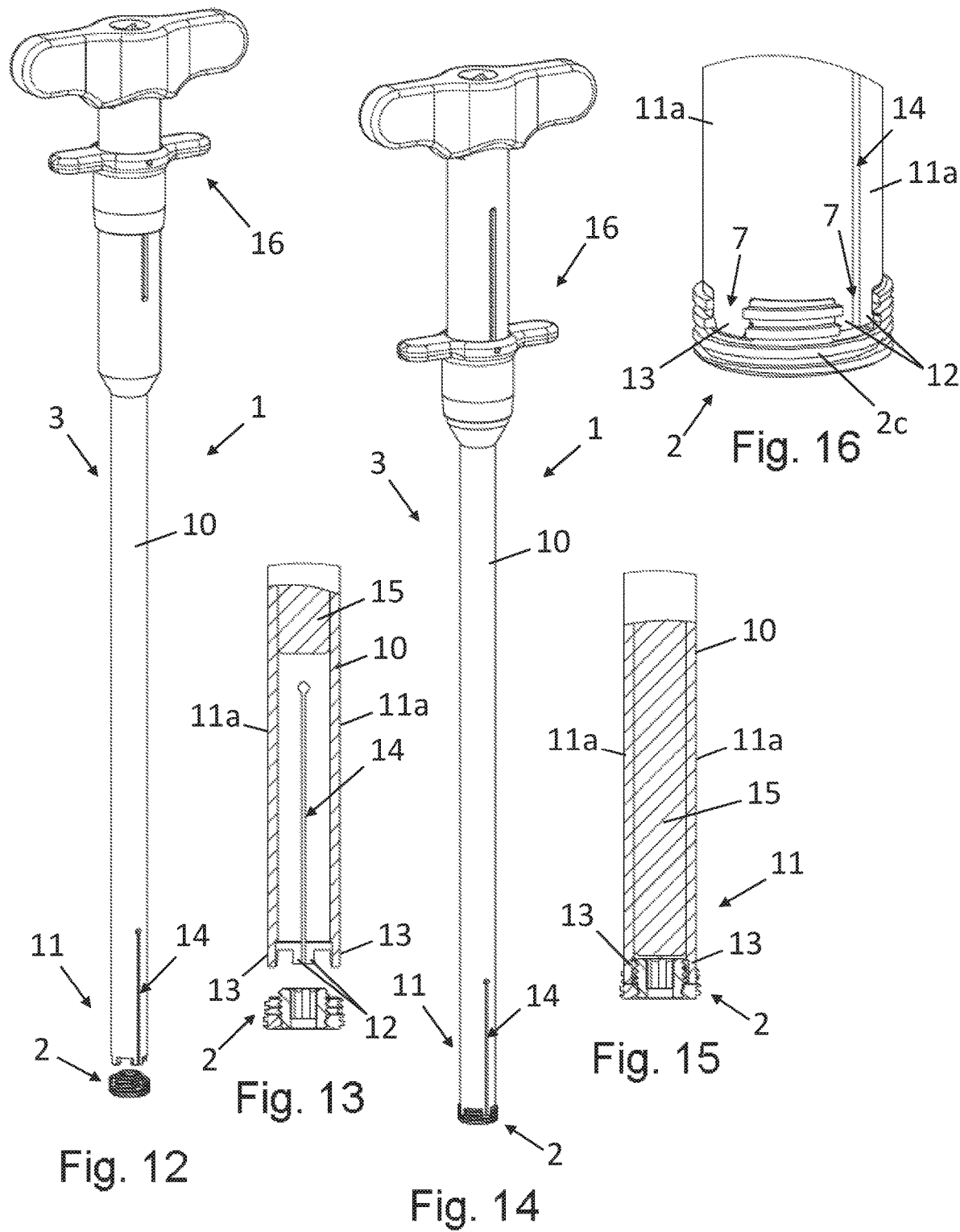

SURGICAL ASSEMBLY FOR PLACING A PEDICLE-SCREW CAP

RELATED APPLICATIONS

This application is a National Phase of PCT Patent Application No. PCT/FR2016/052049 having International filing date of Aug. 8, 2016, which claims the benefit of priority of French Patent Application No. 1557966 filed on Aug. 27, 2015. The contents of the above applications are all incorporated by reference as if fully set forth herein in their entirety.

FIELD AND BACKGROUND OF THE INVENTION

The present invention relates to the technical sector of surgical instruments and more specifically relates to a surgical assembly for the placement of a cap in a pedicle screw, in particular for treatment of spinal pathologies.

In general, a spinal implant comprises at least two pedicle screws intended to be screwed on a variable anatomical element of the vertebra (e.g. lamina, pedicle, vertebral body) and a connection system (plate or rod) uniting the two pedicle screws to each other.

Using a threaded cap suited for screwing into the head of the pedicle screw and for holding a connecting rod in place is well known. The cap used comes either in the form of a single cap comprising an external thread, and a central recess for tightening comprising, for example, a connection for a star screw-bit, or else in the form of a double cap comprising an inner cap and an outer cap screwed one into the other. The inner cap comprises a central hollow for tightening and an outer thread, and the outer cap comprises an inner thread and an outer thread and recesses for tightening.

Instruments for placement of these caps are also known. These instruments form, for example, a set generally comprising the cap as such and a cap-holder. The instruments are in particular designed for surgical operations referred to as minimally invasive, during which the surgeon is unable to view the implants.

A surgical assembly comprising a cap and a cap-holder is known from the state of the art, in particular disclosed in the document US 2011166610. The cap-holder includes two elastic and diametrically opposed longitudinal branches surrounded by a sliding sleeve. The branches each comprise an inner tang opposite from each other. The cap comprises two diametrically opposed radial grooves arranged in an outer lateral wall of said cap. The two grooves each comprise a recess complementary to the tang of the branches, laid out toward the inside of the cap.

In order to carry the cap, the two branches enter, by deforming elastically, into the grooves with the tangs thereof by engaging in the complementary recesses for holding the cap. The sleeve of the cap-holder is slid toward the cap for preventing the elastic branches from separating from each other and locking the connection between the cap-holder and the cap.

A cap and cap-holder is also known, in particular disclosed in the document US 2012123431. The cap comprises a central recess with an inner annular groove. The cap-holder comprises a hollow sleeve having a plurality of longitudinal slits defining elastic branches. The elastic branches each comprise a bead extending towards the outside of the sleeve, able to come to house, by elastic deformation of the branches, inside the annular groove of the cap. With the insertion of a locking pin in the hollow sleeve, the connection between the cap-holder and the cap is locked by blocking the elastic branches from coming closer.

A disadvantage of the surgical assemblies from the prior art described above resides in the fact that they cannot adapt to the two cap types, single or double, by allowing both the screwing of the inner cap and the screwing of the outer cap. In fact, the state of the art described above does not allow the surgeon to exert through the cap-holder a meaningful tightening torque on the cap, whatever the type thereof.

SUMMARY OF THE INVENTION

One of the goals of the invention is therefore to remedy at least the aforementioned drawbacks by proposing a surgical assembly for placement of a single or double cap in a pedicle screw, for which the connection between the cap and the cap-holder is relatively secured for avoiding the risks of disconnection during the placement of the cap, allowing a simpler in situ reconnection of the cap and cap-holder, all while being sufficiently resistant for allowing the surgeon to exert, via the cap-holder, a significant tightening torque on the cap, specifically at least equivalent to 5 N-m.

Another object of the present invention is to reinforce the locking between the cap and the cap-holder and to further secure the connection thereof.

For this purpose, a surgical assembly was perfected comprising:
  a pedicle-screw cap, where the cap comprises at least one external thread and a central recess in order to insert a screw bit;
  a cap-holder in the form of a hollow sleeve comprising an end for connection with the cap and a locking pin mounted slidably in the hollow sleeve between a neutral position and a position for locking of the cap.

According to the invention:
  The cap includes at least two diametrically opposed radial notches, provided from one external lateral wall of said cap, each of the notches comprising at least one lateral groove;
  The connection end of the cap-holder sleeve is extended longitudinally by two diametrically opposed lugs which can engage in the notches and each comprising a lateral shoulder complementarity to the groove of the notch and able to engage in said groove for axially locking the sleeve on the cap.

The lateral direction of the grooves and shoulders is understood to mean a direction perpendicular to the radial direction respectively of the cap or sleeve. In that way, with the present invention, a cap can be grasped by means of the cap-holder for placement of the cap in a pedicle screw. In practice, in this embodiment, grasping the cap is done by inserting the lugs of the sleeve into the notches of said cap, and by turning said sleeve in the direction of screwing for engaging the shoulders in the grooves and axially locking the sleeve on the cap. To securely maintain this axial locking, it is appropriate to slide the locking pin into the locking position, meaning until said locking pin comes to exert an axial pressure on the cap for keeping the shoulders engaged in the grooves.

The present invention has the advantage of being able to be practiced with a single cap comprising an outer thread and a central recess for tightening with notches provided around the central recess, or with a double cap comprising notches provided in the outer cap, around the inner cap.

In this way, with the shouldered lugs the surgeon can exert, by means of the cap-holder, a significant tightening torque on the single cap or on the external cap of the double cap, specifically at least a tightening torque equivalent to 5 N-m.

For screwing the inner cap, it is appropriate to disconnect and remove the cap-holder and then insert a screwing member in the tightening recess for screwing it as such.

The connection/disconnection between the cap and the cap-holder is simple. Further, the configuration of the cap-holder is such that it has, in practice, a sleeve comprising a diameter of less than 10 mm so that it can be inserted in an extension tube used for placement of a pedicle screw.

According to a specific embodiment, the grooves of the notches and the shoulders of the lugs are inclined such that rotation of the sleeve in the direction of screwing forces the axial locking.

Advantageously, the notches and lugs each respectively comprise a second opposing lateral groove and a second opposing lateral shoulder, which provides an axial locking of the cap-holder on the cap in the direction of unscrewing of the cap as well.

In this latter configuration, and according to another advantageous embodiment of the invention, the connection end of the sleeve comprises two longitudinal and diametrically opposed slits so as to form two elastic branches, where said slits pass by the lugs forming two pairs of lugs. The lugs from each pair of lugs are able to come to engage, by coming closer to each other by elastic deformation of the branches, in the corresponding notch until the shoulders of the lugs come to latch in the grooves of the notches.

With this configuration, the connection between the cap-holder and the cap can be locked more securely and by latching.

In this configuration, and advantageously, the cap comprises two additional radial notches, diametrically opposed and evenly distributed on either side of the first notches, and the sleeve comprises tightening tabs which longitudinally extend the connection end of the sleeve, and which are diametrically opposed and regularly distributed on either side of the lugs, where said tightening tabs are intended to come snugly engage in the notches to make it easier to screw/unscrew the cap by optimally transmitting to said cap the tightening/untightening torque exerted by the hollow sleeve.

In this embodiment, and in order to further secure the connection between the cap and the cap-holder, the locking pin comprises an outer diameter fitted to the inner diameter of the hollow sleeve, such that in locking position the locking pin is positioned between the elastic branches of the sleeve and prevents the unlocking of the cap-holder by preventing the elastic branches from getting closer and the pairs of lugs from disengaging.

Advantageously, the locking pin is subject in the upper part to a latch for the passage of the locking pin from the neutral position to the locking position.

According to a specific embodiment, the locking pin comprises a screw bit able to come engage, in locking position, in the central recess for screwing the cap.

Thus, the inner cap can be screwed with the locking pin in locking position. It is therefore not necessary to withdraw the cap-holder for screwing the inner cap, or to use a separate tightening member.

According to another advantageous embodiment, the locking pin is hollow and allows insertion of a screwing member in the form of a shaft with a screw bit. Thus, screwing of the inner cap can be done without withdrawing the cap-holder.

Preferably, the tightening tabs are longer than the lugs in order to allow the guiding of the engagement of said lugs in said notches.

As discussed above, the cap has either the shape of a single cap, or the shape of a double cap. In the case of a double cap, the inner cap comprises a lower annular bead forming a stop during unscrewing of the inner cap, or during screwing of the outer cap thus preventing the accidental disassembly of the two caps during the surgical operation.

BRIEF DESCRIPTION OF THE SEVERAL VIEWS OF THE DRAWINGS

Further characteristics and advantages of the invention will become apparent from the description provided below, which is for reference only and is in no way restrictive, with reference to the accompanying figures, wherein:

FIG. 6 is a schematic perspective view of the connection end of the cap-holder according to the invention;

FIG. 7 schematically illustrates in side view the pairs of lugs of the cap-holder before engagement in the notches of a double cap;

FIG. 8 schematically illustrates in side view the tightening tabs of the cap-holder before engagement in the notches of a double cap;

FIG. 9 schematically illustrates in side view the cap-holder connected to the cap, with a specific embodiment of the lugs of said cap-holder;

FIG. 10 is a schematic view similar to that of FIG. 9 showing another possible embodiment of the lugs of the cap-holder;

FIG. 11 schematically illustrates the connection end of the cap-holder and the cap in longitudinal section along the axis A-A shown in FIGS. 9 and 10;

FIG. 12 is a schematic perspective view of the surgical assembly according to the invention, with the locking pin of the cap-holder unlocked;

FIG. 13 is a longitudinal section view of the connection end of the cap-holder with the locking pin in unlocked position;

FIG. 14 is a schematic perspective view of the surgical assembly according to the invention, with the locking pin locked and the cap-holder connected to the cap;

FIG. 15 is a longitudinal section view of the connection end of the cap-holder with the locking pin in locked position;

FIG. 16 is a schematic perspective view illustrating the connection end of the cap-holder connected to the cap.

DESCRIPTION OF SPECIFIC EMBODIMENTS OF THE INVENTION

The invention relates to a surgical assembly (1) for placement of a cap (2) in a pedicle screw, in particular for treatment of pathologies of the spine. The surgical assembly (1) according to the invention comprises the cap (2) as such and the cap-holder (3).

The cap (2) is suited for coming to be screwed into the head of the pedicle screw for keeping a rod in place for connection of at least two pedicle screws.

Figure 1:
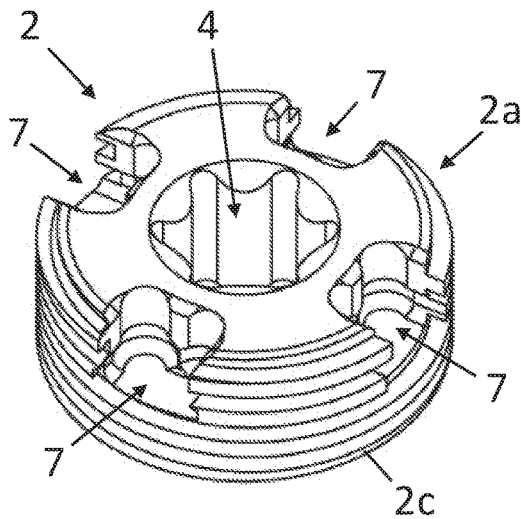
FIG. 1 schematically shows a single cap according to the invention in perspective.
Figure 2:
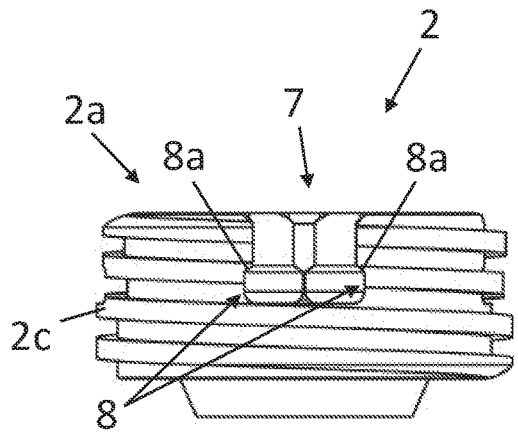
FIG. 2 schematically illustrates the single cap in side view.

For this purpose, and with references to FIGS. 1 to 2, the cap (2) can have the shape of a single cap (2a) comprising an outer thread (2c) able to engage with the head of the pedicle screw, and a central recess (4) for tightening comprising for example a connection for a star screw-bit, for screwing as such of the cap (2).

Figure 3:
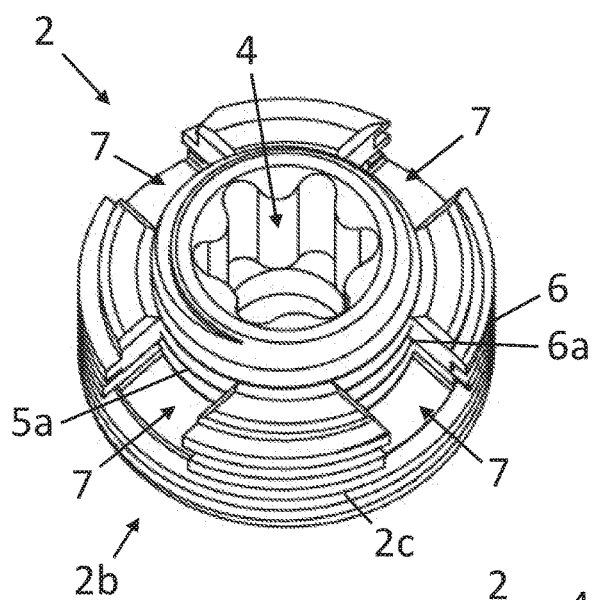
FIG. 3 schematically shows a double cap according to the invention in perspective.
Figure 4:
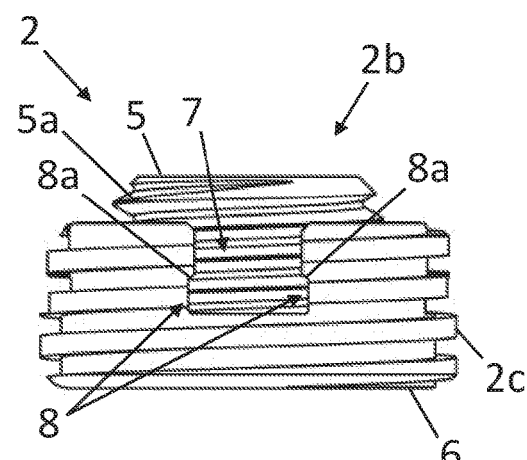
FIG. 4 schematically shows a double cap in perspective side view.

With reference to FIGS. 3 to 4, the cap (2) can also have the shape of a double cap (2b) comprising an inner cap (5) and an outer cap (6) screwed together. The inner cap (5) comprises the central recess (4) for connection and an outer thread (5a) for engaging with the outer cap (6); and, the outer cap (6) comprises an inner thread (6a) for engaging with the inner cap (5) and the outer thread (2c) for engaging with the pedicle screw.

According to a preferred embodiment of the invention, both cap (2) types comprise four identical radial notches (7) uniformly distributed around the circumference of said cap (2), and arranged from an outer lateral wall of said cap (2). In the case of a single cap (2a), the notches (7) are laid out around the central recess (4), and in the case of the double cap (2b) they are laid out in the outer cap (6), around the inner cap (5).

Each notch (7) comprises two lateral grooves (8), meaning laid out in a wall of the notch (7) perpendicular to the radial direction of the cap (2). The grooves (8) comprise an upper flat (8a) inclined towards a lower part of the cap (2).

Figure 5:
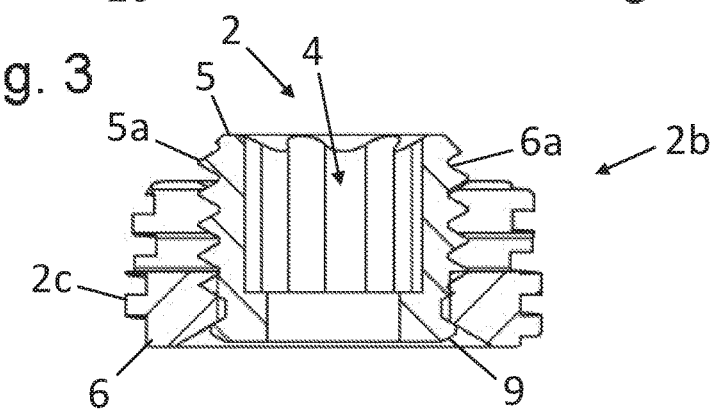
FIG. 5 schematically illustrates the double cap in longitudinal section.

With reference to FIG. 5 and in the case of a double cap (2b), the inner cap (5) comprises a lower annular bead (9) forming a stop during unscrewing of the inner cap (5), or during screwing of the outer cap (6) thus preventing the accidental disassembly of the two caps (2) during the surgical operation.

With reference to FIGS. 6 to 8, the cap-holder (3) comprises a hollow sleeve (10) comprising one end for connection (11) with the cap (2). The connection end (11) of the sleeve (10) is extended longitudinally by two diametrically opposed lugs (12) and by two tightening tabs (13), also diametrically opposed and uniformly distributed on either side of the lugs (12).

The connection end (11) further comprises two longitudinal slits (14) diametrically opposed so as to form two elastic branches (11a). The slits (14) are laid out so as to separate the lugs (12) in two pairs of lugs (12). Each lug (12) comprises a lateral shoulder (12a) complementary to the groove (8) of the notch (7).

In this way, and with reference to FIG. 7, the lugs (12) from each pair of lugs (12) are able to come to engage, by coming closer to each other by elastic deformation of the branches (11a), in the corresponding notch (7) until the shoulders (12a) of the lugs (12) come to latch in the grooves (8). The connection between the cap-holder (3) and the cap (2) is locked securely and by latching.

Similarly, the two tightening tabs (13) are each intended to come to engage in a corresponding notch (7). The width of the tightening tabs (13) in particular corresponds substantially to the width of the notches (7) such that the tightening tabs (13) engage snugly. The tightening tabs (13) are longer than the lugs (12) in order to engage first in the notches (7) and to serve to guide the insertion of the lugs (12). The tightening tabs (13) serve to optimally transmit the tightening/untightening torque exerted by the hollow handle (10) to the cap (2). In particular, with this configuration, a meaningful tightening torque can be exerted on the cap (2), specifically at a minimum a tightening torque equivalent to 5 N-m. According to the invention, the tightening torque can be transmitted just as well to a single cap (2a) as to the external cap (6) of the double cap (2b).

Because the four notches (7) are identical, the cap-holder (3) can connect to the cap (2) more easily, in particular in situ. In fact, each lug (12) and each tightening tab (13) can engage with any one of the four notches (7), which provides four possible connection positions.

Referring to FIGS. 12 to 16, the cap-holder (3) includes a locking pin (15) mounted slidably in the hollow sleeve (10) between a neutral position and a locking position of the cap (2). The locking pin (15) comprises an outer diameter fitted to the inner diameter of the hollow sleeve (10) and is subject in the upper part to a latch (16) for the passage of the locking pin (15) from the upper neutral position (FIGS. 12 and 13) in which it does not prevent the elastic branches (11a) of the hollow sleeve (10) from coming closer, to a lower locking position (FIGS. 14 and 15), towards the cap (2), in which it prevents the unlocking of the cap-holder (3) by preventing the elastic branches (11a) from coming closer and the pairs of lugs (12) from disengaging. Referring to FIG. 16, when the cap-holder (3) is connected to the cap (2), the tightening tabs (13) and the lugs (12) are engaged in the notches (7) and it is possible to tighten the cap (2).

In a specific embodiment shown in FIGS. 9 to 11, the hollow sleeve (10) of the cap-holder (3) comprises four lugs (12) uniformly distributed around the circumference of the hollow sleeve (10) and does not comprise tightening tabs, or longitudinal slits. Grasping the cap (2) is done by inserting the lugs (12) into the notches (7) of said cap (2), and by turning said sleeve (10) in the screwing direction for axially locking the sleeve (10) on the cap (2). To securely maintain this axial locking, it is appropriate to slide the locking pin (15) into the locking position, meaning until said locking pin (15) exerts axial pressure on the cap (2) for keeping the shoulders (12a) of the lugs (12) engaged in the grooves (8) of the notches (7). Advantageously, the shoulders (12a) of the lugs (12) are inclined in order to come to rest against the inclined flats (8a) of the grooves (8) such that the rotation of the sleeve (10) in the direction of screwing forces the axial locking.

According to a specific embodiment shown in FIG. 10, the flats (8a) of the grooves (8) can be inclined so as to form dovetail locking systems, suited for engaging with the complementary dovetail shoulders (12a) of the hollow sleeve (10). In this embodiment, to assure the locking of the sleeve (10) on the cap (2), it is appropriate to turn the sleeve (10) in the screwing or unscrewing direction for lining up the dovetail shapes and to exert a pressure on the cap (2) with the locking pin (15) for engaging said dovetail shapes and preventing the unlocking of the cap (2).

According to another embodiment, not shown, the locking pin (15) comprises a screw bit able to come engage, in locking position, in the central recess (4) for screwing the cap (2).

In practice, for disconnecting the cap-holder (3) from the cap (2), it is appropriate to slide the locking pin (15) into neutral position by actuating the latch (16), possibly rotating the sleeve (10) for the embodiments shown in FIGS. 9 and 10, and pulling either side of the cap-holder (3) and the cap (2) for separating them from each other. When the cap (2) is screwed and attached in the pedicle screw, it is appropriate to simply, after having slid the locking pin (15) into neutral position, pull on the cap-holder (3). In the embodiment shown in FIG. 7, the inclined flats of the shoulders (12a) of the lugs (12) serve to exert a force on the elastic branches (11a) tending to bring them closer together. In this way, the pairs of lugs (12) can disengage from the notches (7). Similarly, the shoulders (12a) are inclined to allow the elastic branches (11a) to come closer when the lugs (12) are engaged in the notches (7).

As can be seen from the preceding, the invention provides a surgical assembly (1) for placing a single cap (2a) or double cap (2b) into a pedicle screw, for which the connection between the cap (2) and cap-holder (3) is made stronger and secure because of the latching of the tabs (12) and the locking that the locking pin (15) provides. Risks of separation during placement of the cap (2) are thereby avoided. The surgical assembly (1) according to the invention allows an easier in situ reconnection of the cap (2) and the cap-holder (3), while also providing a sufficiently resistant connection for allowing a surgeon to exert, with the cap-holder (3), a meaningful tightening torque on the single cap (2a) or on the outer cap (6) of the double cap (2b), specifically at least equivalent to 5 N-m.

What is claimed is:

1. A surgical assembly (1), comprising:
   a pedicle-screw cap (2), where the cap (2) comprises at least one external thread (2c) and a central recess (4) in order to insert a screw bit;
   a cap-holder (3) in the form of a hollow sleeve (10) comprising an end for connection (11) with the cap (2) and a locking pin (15) mounted slidably in the hollow sleeve (10) between a neutral position and a position for locking of the cap (2),
   wherein:
   the cap (2) includes at least two diametrically opposed radial notches (7), provided from one external lateral wall of said cap (2), each of the notches (7) comprising at least one lateral groove (8);
   the connection end (11) of the cap-holder (3) sleeve (10) is extended longitudinally by two diametrically opposed lugs (12) which can engage in the notches (7) and each comprising a lateral shoulder (12a) complementarity to the groove (8) of the notch (7) and able to engage in said Groove (8) for axially locking the sleeve (10) on the cap (2)
   wherein the notches (7) and lugs each comprise a second opposing lateral groove (8), and the lugs (12) each comprise a second opposing lateral shoulder (12a);
   wherein the connection end (11) of the sleeve (10) comprises two longitudinal and diametrically opposed slits (14) so as to form two elastic branches (11a), where said slits (14) pass by the lugs (12) forming two pairs of lugs (12), where the lugs (12) from each pair of lugs (12) are able to come to engage, by coming closer to each other by elastic deformation of the branches (11a), in the corresponding notch (7) until the shoulders (12a) of the lugs (12) come to latch in the grooves (8) of the notches (7).

2. The surgical assembly (1) according to claim 1, wherein the grooves (8) of the notches (7) and the shoulders (12a) of the lugs (12) are inclined such that rotation of the sleeve (10) in the direction of screwing forces the axial locking.

3. The surgical assembly (1) according to claim 1, wherein the cap (2) comprises two additional radial notches (7), diametrically opposed and evenly distributed on either side of the first notches (7), and the sleeve (10) comprises tightening tabs (13) which longitudinally extend the connection end (11) of the sleeve (10), and which are diametrically opposed and regularly distributed on either side of the lugs (12), where said tightening tabs (13) are intended to come snugly engage in the notches (7).

4. The surgical assembly (1) according to claim 1, wherein the locking pin (15) comprises an outer diameter fitted to the inner diameter of the hollow sleeve (10), such that in locking position the locking pin is positioned between the elastic branches (11a) of the sleeve (10) and prevents the unlocking of the cap-holder (3) by preventing the elastic branches (11a) from getting closer and the pairs of lugs (12) from disengaging.

5. The surgical assembly (1) according to claim 1, wherein the locking pin (15) is subject in the upper part to a latch (16) for the passage of the locking pin (15) from the neutral position to the locking position.

6. The surgical assembly (1) according to claim 1, wherein the locking pin comprises a screw bit able to come engage, in locking position, in the central recess (4) for screwing the cap (2).

7. The surgical assembly (1) according to claim 3, wherein the tightening tabs (13) are longer than the lugs (12) in order to serve to guide the insertion of the lugs (12) into the notches (7).

8. The surgical assembly (1) according to claim 1, wherein the cap (2) is made up of two caps screwed into each other, where an outer cap (6) comprises the notches (7), and an inner cap (5) comprises the central recess (4) for screwing.

* * * * *